United States Patent
Somani et al.

(10) Patent No.: US 6,346,530 B1
(45) Date of Patent: Feb. 12, 2002

(54) PROCESS FOR THE PREPARATION OF A BIOAVAILABLE ORAL DOSAGE FORM OF CEFUROXIME AXETIL

(75) Inventors: Jitendra Krishan Somani, Haryana; Indu Bhushan, New Delhi; Himadri Sen, Haryana, all of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/366,986

(22) Filed: Aug. 4, 1999

(30) Foreign Application Priority Data

Mar. 19, 1999 (IN) .................................................. 453/99

(51) Int. Cl.⁷ .............................................. A61K 31/54
(52) U.S. Cl. .................................................... 514/226.8
(58) Field of Search ...................... 514/226.8

(56) References Cited

U.S. PATENT DOCUMENTS 4,267,320 A    5/1981  Gregson et al.
4,865,851 A  * 9/1989  James et al. ................. 424/498
5,063,224 A  * 11/1991 Mosher et al. .............. 514/202
5,847,118 A  * 12/1998 Karimian et al. ........... 540/222
6,060,599 A  * 5/2000  Somani et al. .............. 540/222

OTHER PUBLICATIONS

Indian Patent Application No. 2235/Del/98 filed Jul. 31, 1998 entitled "Process For Preparing A Highly Pure, Predominantly Amorphous Form of Cefuroxime Axetil".

* cited by examiner

*Primary Examiner*—William R. A. Jarvis
*Assistant Examiner*—Vickie Kim
(74) *Attorney, Agent, or Firm*—Jayadeep R. Deshmukh, Esq.

(57) ABSTRACT

This invention relates to a process of mixing of crystalline cefuroxime axetil with amorphous cefuroxime axetil for the preparation of a bioavailable oral dosage form comprising of amorphous cefuroxime axetil containing from 7 to 25% crystalline cefuroxime axetil.

6 Claims, No Drawings

PROCESS FOR THE PREPARATION OF A BIOAVAILABLE ORAL DOSAGE FORM OF CEFUROXIME AXETIL

FIELD OF THE INVENTION

This invention relates to a process of mixing of crystalline cefuroxime axetil with amorphous cefuroxime axetil for the preparation of a bioavailable oral dosage form comprising of amorphous cefuroxime axetil containing from 7 to 25% crystalline cefuroxime axetil.

BACKGROUND OF THE INVENTION

Cefuroxime axetil is a 1-acetoxyethyl ester of cefuroxime. It is a second generation cephalosporin antibiotic with a broad spectrum of activity against gram-positive and gram-negative microorganisms. This compound as well as many other esters of cefuroxime are disclosed and claimed in U.S. Pat. No. 4,267,320.

Crystalline cefuroxime axetil, however, does not exhibit adequate bioavailability upon oral administration. It is important that cephalosporin compounds for oral administration should be in a form which provides high bioavailability whereby absorption into the blood stream is maximized and the amount of antibiotic remaining in the gastrointestinal tract is minimized. Any antibiotic which is not absorbed will be therapeutically ineffective and by remaining in the gastrointestinal tract may cause side effects. An amorphous form of cefuroxime axetil which has high bioavailability has been described in U.S. Pat. No. 4,562,181. This form is essentially free from crystalline material. Related U.S. Pat. Nos. 4,820,833, 4,994,567, and 5,013,833 describe processes for the preparation of amorphous cefuroxime axetil.

U.S. Pat. No. 4,820,833 claims a process for preparing a highly pure, substantially amorphous form of cefuroxime axetil which comprises preparing a highly pure solution of cefuroxime axetil and spray drying it to recover highly pure substantially amorphous cefuroxime axetil.

U.S. Pat. No. 4,994,467 claims a process for the preparation of predominantly pure amorphous cefuroxime axetil which comprises recovering cefuroxime axetil from a solution thereof by roller drying.

U.S. Pat. No. 5,103,833 claims a process for the preparation of highly pure cefuroxime axetil in a predominantly amorphous form by solvent precipitation. The solvents claimed, however, require elevated temperatures for dissolving cefuroxime axetil.

Although solvent precipitation is a cheap and commercially viable method of preparing amorphous cefuroxime axetil, it suffers from the disadvantages of not yielding highly pure amorphous cefuroxime axetil, a form which is known to have high bioavailability. It is for this reason that the commercially available formulation of cefuroxime axetil, "Ceftin™", marketed by Glaxo is formulated from highly pure amorphous cefuroxime axetil produced by the spray drying method which is a very expensive process involving huge capital investments. Although highly pure amorphous cefuroxime axetil has been reported to have a higher bioavailability than crystalline cefuroxime axetil, it needs careful processing and cannot be processed by the commonly used wet granulation technique as the amorphous form gets converted to the crystalline form upon contact with water.

According to the present invention, we have studied the effect of different percentage of crystallinity in the amorphous cefuroxime axetil on the bioavailability of cefuroxime axetil formulations when compared with a formulation made up of highly pure amorphous cefuroxime axetil. Surprisingly, we found that tablets containing from 7 to 25% crystalline cefuroxime axetil together with amorphous cefuroxime axetil exhibited similar bioavailability profile as the tablets composed of pure amorphous cefuroxime axetil. This not only allows more flexibility in choosing the wet granulation technique for processing without fear of generating a small percentage of crystallinity in the tablet, it also allows the use of the cheaper and more commercially viable method of solvent precipitation of preparing predominantly amorphous cefuroxime axetil, which may contain up to 10% crystallinity as described in copending Indian application No. 2235/Del/98.

According to another aspect of the invention a sodium salt of citric acid, monosodium citrate, is added to the formulation containing cefuroxime axetil with different percentages of crystallinity. It is known in the art that when amorphous cefuroxime axetil comes in contact with water, it forms a gel which prolongs the disintegration and retards the dissolution in a tablet formulation. This property to form a gel is dependent upon the temperature, pH and ionic strength of the media. To get an optimum dissolution profile from the tablet, it is essential to reduce the ability of amorphous cefuroxime axetil to form a gel. We have observed that addition of a sodium salt of citric acid to the formulation containing amorphous cefuroxime axetil inhibits the tendency of amorphous cefuroxime axetil to form a gel. This may be due to the presence of citrate ions which prevents cefuroxime axetil molecules from bridging to form a gel, thereby helping in tablet dissolution.

These results are further illustrated by the examples described herein.

DETAILED DESCRIPTION OF THE INVENTION

To check the effect of percentage crystallinity on the bioavailability of cefuroxime axetil, amorphous cefuroxime axetil prepared by the process described in our copending application containing 12% crystallinity was formulated as given in Example 1.

EXAMPLE 1

TABLE 1.1

| Ingredient s | Mg/tablet |
| --- | --- |
| Cefuroxime Axetil | 625.0 |
| (12% Crystalline) | (equal To 500 mg cefuroxime axetil) |
| Sodium Lauryl Sulfate | 50.0 |
| Colloidal Silicon dioxide | 10.0 |
| Microcrystalline cellulose | 45.0 |
| Calcium carbonate | 15.0 |
| Croscarmellose sodium | 180.0 |
| Sucrose | 80.0 |
| Povidone | 35.0 |
| Monosodium Citrate | 50.0 |
| Stearic acid | 10.0 |
| Total weight | 1100.0 |

Amorphous cefuroxime axetil (containing 12% crystallinity), microcrystalline cellulose, sodium lauryl sulfate, colloidal silicon dioxide, croscarmellose sodium and calcium carbonate were sifted through British Standard sieve (BSS) mesh size 22. Sucrose and povidone were also sifted through BSS mesh 22 and dissolved in water to prepare the binder solution. Binder solution was added to the premix in a RMG and the mass was granulated. The granules were dried in a fluid bed drier. The granules were sifted through BSS #42. Remaining ingredients were passed through BSS #60 and mixed for 10 minutes. The granules were then compacted to tablets.

Dissolution Profile: Dissolution of tablets was carried out in 900 ml of 0.07 N HCl at 37° C. in USP apparatus II.

TABLE 1.2

| Time | Cumulative percent drug released |
|------|----------------------------------|
| 15   | 63.0                             |
| 30   | 72.0                             |
| 45   | 77.0                             |

Tablets formulated without monosodium citrate did not disintegrate even after 45 minutes in the buffer due to gel formation by the drug.

In the next experiment, 20% crystalline cefuroxime axetil was physically mixed with amorphous cefuroxime axetil and tabletted as described in Example 2:

Dissolution Profile: Dissolution was carried out in 900ml of 0.07ml of 0.07 N HCI at 37° C. in USP apparatus II.

TABLE 2.2

| Time | Cumulative percent drug released |
|------|----------------------------------|
| 15   | 60.0                             |
| 30   | 66.0                             |
| 45   | 68.0                             |

Once again same formulation prepared without monosodium citrate formed a gel and did not disintegrate even after 45 minutes.

The bioavailability of these formulations was then compared with composed of pure amorphous cefuroxime axetil. Table 3 gives the results of the comparison of bioavailability studies carried out on the formulations described in Example 1 and 2 and Glaxo's Ceftin™ formulation.

TABLE 3

COMPARISON OF THE PHARMACOKINETIC PARAMETERS

| Product/Statics | $C_{max}$ (mcg/ml) | AUC 0-t (mcg.h/ml) | AUC O-u (mcg.h/ml) | Tmax (h) |
|---|---|---|---|---|
| Example 1 (A) (1100 mg) | 5.70 | 19.18 | 19.79 | 1.64 |
| Example 2 (B) (1300 mg) | 5.60 | 18.61 | 19.41 | 2.0 |
| Glaxo: Ceftin 500 | 6.02 | 19.08 | 19.94 | 1.98 |
| Ratio of least Square Mean | | | | |
| A/R (%) | 100.02 | 96.42 | 96.44 | |
| (90% confidence interval) | (94.08–106.34) | (90.58–102.64) | (91.89–108.11) | |
| B/R (%) | 94.0 | 97.4 | 97.0 | |
| (90% Confidence interval) | (82.1–107.7) | (83.3–113.8) | (82.2–114.5) | |

EXAMPLE 2

TABLE 2.1

| Ingredients | Mg/tablet |
|---|---|
| Cefuroxime Axetil (20% Crystalline) | 635.0 (equal To 500 mg cefuroxime axetil) |
| Sodium Lauryl Sulfate | 51.0 |
| Colloidal Silicon dioxide | 10.0 |
| Microcrystalline cellulose | 203.0 |
| Calcium carbonate | 15.0 |
| Croscarmellose sodium | 212.0 |
| Sucrose | 120.0 |
| Povidone | 40.0 |
| Stearic acid | 14.0 |
| Total weight | 1300.0 |

Cefuroxime axetil, microcrystalline cellulose, sodium lauryl sulfate, colloidal silicon dioxide, croscarmellose sodium and calcium carbonate were sifted through British Standard sieve (BSS) mesh size 22. Sucrose and povidone were also sifted through BSS mesh 22 and dissolved in water to prepare the binder solution. Binder solution was added to the premix in a RMG and the mass was granulated. The granules were dried in a fluid bed drier. The granules were sifted through BSS #42. Remaining ingredients were passed through BSS #60 and mixed for 10 minutes. The granules were then compacted to tablets.

The bioavailability studies were carried out in 12 volunteers under fasting conditions. The Cmax, AUC 0-t, and AUC 0-α for both the formulations A and B containing 12 and 20% crystalline cefuroxime axetil respectively, are very close to those obtained from the Ceftin™ formulation of cefuroxime axetil composed of pure amorphous cefuroxime axetil.

While the present invention has been described in terms of its specific embodiments, certain modifications and equivalents will be apparent to those skilled in the art and are intended to be included within the scope of the present invention.

We claim:

1. A process for the preparation of an oral dosage form comprising mixing of amorphous cefuroxime axetil with crystalline cefuroxime axetil such that crystalline cefuroxime axetil forms from about 7 to about 25 weight percent of the total amount of amorphous cefuroxime axetil together with crystalline cefuroxime axetil, wherein the dosage form comprising the mixture of crystalline and amorphous cefuroxime axetil exhibited a comparable bioavailability profile as pure amorphous cefuroxime axetil.

2. A process for the preparation of an oral dosage form as described in claim 1 comprising cefuroxime axetil as the active moiety and pharmaceutically acceptable excipients wherein at least one excipient is a sodium salt of citric acid.

3. A process as described in claim 2 wherein the sodium salt of citric acid is present in an amount upto 20% of the dosage form.

4. A process as described in claim 2 and 3 wherein the sodium salt of citric acid is monosodium citrate.

5. A process as described in claim 1 wherein the oral dosage form is a tablet.

6. A process as described in claim 1 wherein the tablet is prepared by wet granulation.

* * * * *